United States Patent
Amin et al.

(10) Patent No.: US 7,257,287 B2
(45) Date of Patent: *Aug. 14, 2007

(54) OPTICAL INTERLEAVER

(75) Inventors: Jaymin Amin, Corning, NY (US);
Mark F. Krol, Painted Post, NY (US);
Qi Wu, Eatontown, NJ (US)

(73) Assignee: Avanex Corporation, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/967,113

(22) Filed: Oct. 15, 2004

(65) Prior Publication Data

US 2005/0135737 A1 Jun. 23, 2005

Related U.S. Application Data

(60) Division of application No. 10/112,624, filed on Mar. 28, 2002, now Pat. No. 6,956,988, which is a continuation-in-part of application No. 10/103,469, filed on Mar. 20, 2002, now abandoned, which is a continuation of application No. 09/356,217, filed on Jul. 16, 1999, now Pat. No. 6,370,286.

(60) Provisional application No. 60/279,695, filed on Mar. 30, 2001, provisional application No. 60/279,696, filed on Mar. 30, 2001, provisional application No. 60/097,464, filed on Aug. 21, 1998.

(51) Int. Cl.
*G02B 6/28* (2006.01)
*G02B 6/293* (2006.01)
*G02B 5/30* (2006.01)

(52) U.S. Cl. .......................... 385/24; 385/11; 359/484; 359/494

(58) Field of Classification Search .................. 385/15, 385/16, 24; 398/48–51, 79–83
See application file for complete search history.

(56) References Cited

U.S. PATENT DOCUMENTS

| | | | |
|---|---|---|---|
| 4,566,761 A | 1/1986 | Carlsen et al. | |
| 4,685,773 A | 8/1987 | Carlsen et al. | |
| 4,756,607 A | 7/1988 | Watanabe et al. | |
| 4,801,189 A | 1/1989 | Shaw et al. | |
| 4,974,944 A | 12/1990 | Chang | |
| H1155 H | 3/1993 | Fratello et al. | |
| 5,428,477 A | 6/1995 | Siroki | |
| 5,774,264 A | 6/1998 | Konno et al. | |
| 6,040,932 A | 3/2000 | Duck et al. | |
| 6,169,626 B1 | 1/2001 | Chen et al. | |
| 6,243,200 B1 | 6/2001 | Zhou et al. | |
| 6,370,286 B1 | 4/2002 | Krol et al. | |
| 6,674,968 B1 * | 1/2004 | Xie | 398/79 |
| 6,956,988 B2 * | 10/2005 | Amin et al. | 385/24 |
| 2001/0042821 A1 | 11/2001 | Zhou et al. | |
| 2001/0050814 A1 | 12/2001 | Zhao | |
| 2001/0053025 A1 | 12/2001 | Zhao | |
| 2001/0055134 A1 | 12/2001 | Zhao | |
| 2001/0055158 A1 | 12/2001 | Zhao | |
| 2002/0159151 A1 * | 10/2002 | Li | 359/498 |
| 2002/0181102 A1 * | 12/2002 | Leyva et al. | 359/495 |

FOREIGN PATENT DOCUMENTS

CA 2203729 10/1998

(Continued)

*Primary Examiner*—Michelle Connelly-Cushwa
(74) *Attorney, Agent, or Firm*—Patterson & Sheridan, LLP (57) ABSTRACT

In accordance with an exemplary embodiment of the present invention, an optical device includes an interleaver/deinterleaver, which includes a passive thermal compensator, wherein an optical signal which transverses the optical device undergoes substantially no temperature induced frequency drift over a desired temperature range.

21 Claims, 5 Drawing Sheets

FOREIGN PATENT DOCUMENTS

| | | |
|---|---|---|
| EP | 0 220 691 | 5/1987 |
| EP | 0 177 800 | 4/1988 |
| EP | 0 362 900 | 4/1990 |
| EP | 0 874 489 | 10/1998 |
| EP | 1 152 265 A2 | 11/2001 |
| EP | 1 178 347 A2 | 2/2002 |
| WO | 99/47956 | 9/1999 |
| WO | 00/11510 | 3/2000 |
| WO | 00/22741 | 4/2000 |
| WO | WO 01/39380 A2 | 5/2001 |
| WO | WO 01/67143 A1 | 9/2001 |

* cited by examiner

OPTICAL INTERLEAVER

CROSS-REFERENCE TO RELATED APPLICATIONS

This application is a divisional of U.S. patent application Ser. No. 10/112,624, filed Mar. 28, 2002 now U.S. Pat. No. 6,956,988, which is herein incorporated by reference in its entirety.

U.S. patent application Ser. No. 10/112,624 is a continuation-in-part application under 35 USC § 120 of U.S. patent application Ser. No. 10/103,469 filed Mar. 20, 2002 and entitled "Tunable Optical Filter," now abandoned, which is a continuation of U.S. patent application Ser. No. 09/356,217 filed Jul. 16, 1999, now U.S. Pat. No. 6,370,286, issued Apr. 9, 2002, which claims the benefit of U.S. Provisional Application No. 60/097,464, filed Aug. 21, 1998. The present application also claims priority under 35 USC § 119(e) from U.S. Provisional Application Ser. Nos. 60/279,695 and 60/279,696, entitled "Optical Interleaver", and "Optical Interleaver With Passive Thermal Effect Compensation," respectively, and filed on Mar. 30, 2001. The disclosures of all of the above referenced patent applications and provisional applications, except the disclosure of U.S. Provisional Application No. 60/097,464, are specifically incorporated herein by reference as though reproduced in their entirety herein.

FIELD OF THE INVENTION

The present invention relates generally to optical communications, and particularly to an optical interleaver/deinterleaver.

BACKGROUND OF THE INVENTION

The increasing demand for high-speed voice and data communications has led to an increased reliance on optical communications, especially optical fiber communications. The use of optical signals as a vehicle to carry channeled information at high speed is preferred in many instances to carrying channeled information at other electromagnetic wavelengths/frequencies in media such as microwave transmission lines, coaxial cable lines, and twisted copper pair transmission lines.

Advantages of optical media include higher channel capacities (bandwidth), greater immunity to electromagnetic interference, and lower propagation loss. In fact, it is common for high-speed optical systems to have signal rates in the range of approximately several megabits per second (Mbit/s) to approximately several tens of gigabits per second (Gbit/s), and greater. However, as the communication capacity is further increased to transmit greater amounts of information at greater rates over fiber, maintaining signal integrity can be exceedingly challenging.

One way to more efficiently use available resources in the quest for high-speed information transmission is known as multiplexing, in which a plurality of channels are transmitted along an optical waveguide (e.g. an optical fiber). One particular type of multiplexing is wavelength division multiplexing (WDM). In WDM, each high-speed information channel has a center wavelength and prescribed channel bandwidth. At the receiver end, the plurality of optical channels is then separated and may be further processed by electronics. (By convention, when the number of channels transmitted by such a multiplexing technique exceeds approximately four, the technique is referred to as dense WDM or DWDM).

While transmission of information via an optical medium has offered significant improvements in information transmission, increased demand for capacity may still adversely impact signal quality during transmission. For example, the number of channels that can be carried in a single optical fiber is limited by cross-talk, narrow operation bandwidth of optical amplifiers, and optical fiber non-linearities.

Currently, center wavelengths, channel bandwidths and spacing between interleaved channels preferably conform to an International Telecommunication Union (ITU) channel grid. For example, one ITU channel grid has a channel spacing requirement of 100 GHz. In this case, the channel spacing is referenced in terms of a frequency spacing, which corresponds in this example to a channel center wavelength spacing of 0.8 nm. With 100 GHz channel spacing, channel "n" would have a center frequency 100 GHz less than channel "n+1" (or channel "n" would have a center wavelength 0.8 nm greater than the center wavelength of channel "n+1").

As can be appreciated, the more information that is sent over a particular medium, the greater the number of channels that are needed. It follows, that due to bandwidth considerations, the larger the number of channels, and the closer the separation between channels become. Among other difficulties, the decrease in channel spacing makes separating the plurality of optical channels more challenging. For example, in order to preserve the integrity of the signal at the receiver end of the communication link, cross-talk in the form of received channel overlap must be minimized. As can be appreciated, meeting these performance requirements of ever-increasing demand is a technical and practical challenge.

The technical and practical challenges described above are further exacerbated by environmental factors. These environmental factors can adversely impact the performance of the devices. One deleterious environmental factor is the ambient temperature. For example, changes in the ambient temperature can create temperature induced wavelength drift of the WDM. This wavelength drift can cause wavelength channel overlap. In the closely spaced channels of ITU grids discussed above, optical system performance may be adversely impacted.

Accordingly, there is often a need to compensate for temperature fluctuations in WDM systems. While it may be possible to control the ambient temperature surrounding the WDM device, this generally requires rather elaborate climate control devices, which can be relatively complex and expensive. Moreover, these devices do not ensure the particular elements of a WDM are immune to temperature fluctuations. As such, in addition to adding complexity and expense, known active temperature control schemes may be unreliable.

Accordingly, what is needed is an optical interleaver/deinterleaver that caters to immediate and future needs for high speed optical networks without the disadvantages associated with current components and approaches.

SUMMARY OF THE INVENTION

In accordance with an exemplary embodiment, an optical device includes an interleaver/deinterleaver, which includes a passive thermal compensator, wherein an optical signal, which traverses the optical device, undergoes substantially no temperature induced frequency drift over a desired temperature range.

In accordance with another exemplary embodiment of the present invention, an optical interleaver/deinterleaver includes a first element which decomposes said optical signal into a first beam and a second beam with the first beam being in a first polarization state and the second beam being in a second polarization state. The first and second polarization states being orthogonal to one another and including each of said multiple channels. The optical interleaver/deinterleaver further includes a second element which transforms the first beam into a first elliptically polarized state having odd channels in a third polarization state and even channels in a fourth polarization state and the second element transforming the second beam into a second elliptically polarized state having even channels in the third polarization state and odd channels in the fourth polarization state; and a third element which combines the odd channels into a first output port and the even channels into a second output port.

BRIEF DESCRIPTION OF THE DRAWINGS

The invention is understood from the following detailed description when read with the accompanying figures. It is emphasized that the various features in the figures may not necessarily be drawn to scale. In fact, the dimensions of the various features may be arbitrarily increased or decreased for clarity of discussion. Moreover, wherever possible, like reference numerals refer to like elements.

DEFINED TERMS

As used herein "interleaving" refers to combining two or more streams of optical signals, wherein each stream contains a plurality of optical channels; and "deinterleaving" refers to separating an optical signal, which contains a plurality of optical channels, into two or more streams of optical signals, each of which contains a subset of the plurality of optical channels. Generally interleaving decreases the channel spacing between adjacent channels, and de-interleaving increases the channel spacing between adjacent channels.

DETAILED DESCRIPTION

The invention will now be described more fully with reference to the accompanying drawing figures, in which exemplary embodiments are shown. In the following detailed description, for purposes of explanation and not limitation, exemplary embodiments disclosing specific details are set forth in order to provide a thorough understanding of the present invention. However, it will be apparent to one having ordinary skill in the art having had the benefit of the present disclosure, that the present invention may be practiced in other embodiments that depart from the specific details disclosed herein. Moreover, descriptions of well-known devices, methods and materials may be omitted so as to not obscure the description of the present invention.

Briefly, the invention is drawn to a method and apparatus for interleaving/deinterleaving optical signals based on polarization inteferometry. Illustratively, the input optical signal from an input port has a known channel frequency period or channel spacing and the output optical signals from two output ports have a channel frequency period or channel spacing that is an integer even multiple (e.g. two) of that of the input signal. Moreover, the illustrative embodiments herein describe the deinterleaving function. Of course, from the reciprocity principle of optics, the methods and apparati of the exemplary embodiments present invention described herein may be used to achieve an interleaving function. In such a case, the interleaved optical signal would have channel spacing that is an even fraction (e.g. one-half) of the channel spacing of the two input optical signals.

Figure 1:
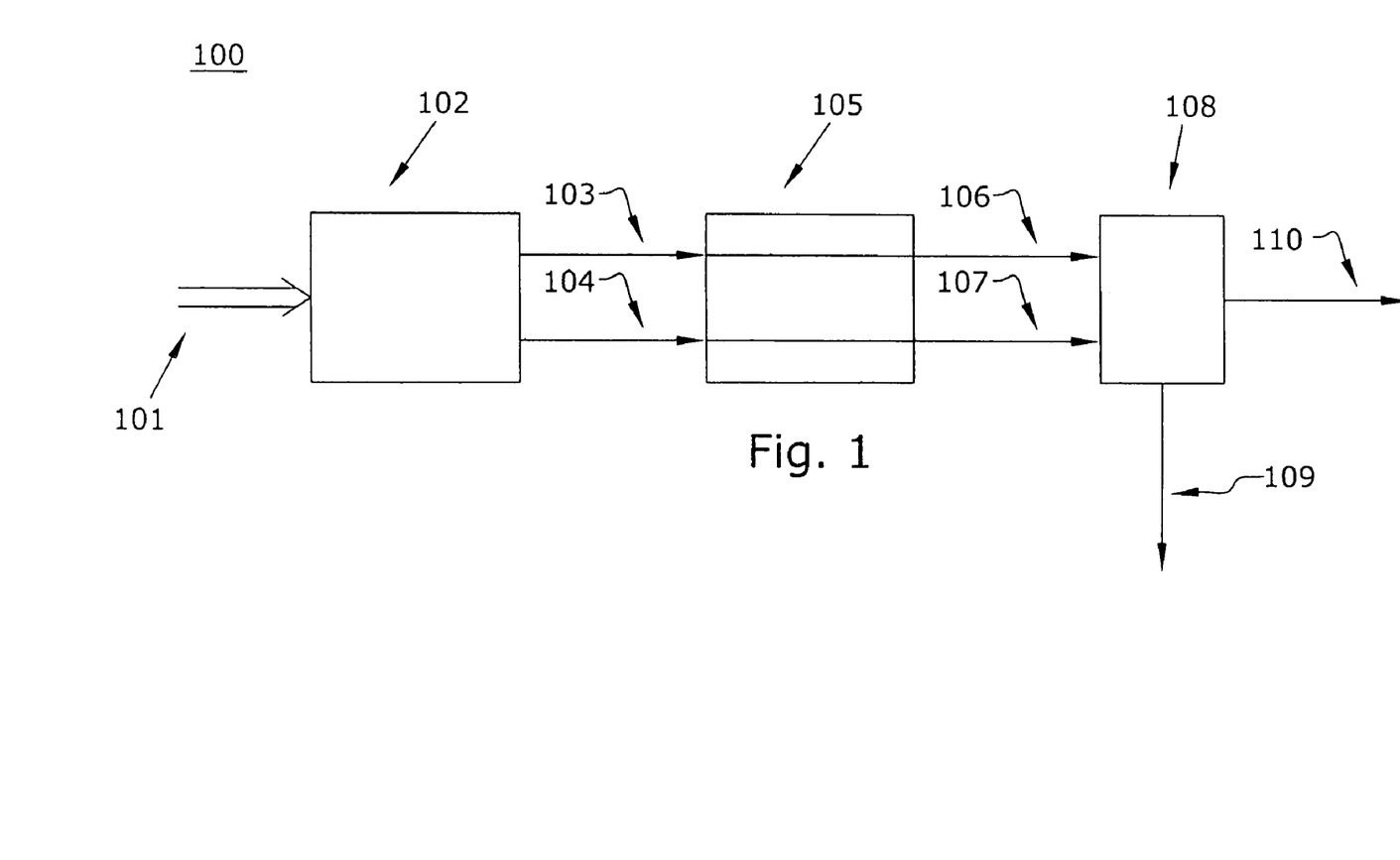
FIG. 1 is a schematic view of an interleaver according to an exemplary embodiment of the present application.

Turning initially to FIG. 1, an interleaver/deinterleaver 100 (hereinafter referred to as interleaver 100) according to an exemplary embodiment of the present invention is shown. An input signal 101 is incident on a first element 102. The input signal 101 is illustratively a multiplexed optical signal having channels 1, 2, . . . n, with respective channel center wavelengths of $\lambda_1, \lambda_2, \ldots \lambda_n$. In the exemplary embodiment of FIG. 1, the input signal 101 is polarized light. The first element 102 separates the polarized light into orthogonal polarization components, which emerge as separate optical beams 103 and 104. Optical beam 103 is linearly polarized light having polarization vectors that are in a first plane. Optical beam 104 is linearly polarized light as well, having polarization vectors that are in a second plane, wherein the first and second planes are mutually orthogonal. Moreover, the first element 102 merely separates the polarization components of the polarized input signal 101, and therefore each optical beam 103 and 104 includes all of the channels 1, 2, . . . n.

Next, a second element 105 transforms optical beams 103 and 104 into polarized beams 106 and 107. Illustratively, polarized beam 106, which is the polarization transformation of optical beam 103, has orthogonal polarization components, with a first polarization state including the odd channels of the input signal (i.e. channels 1, 3, . . . n) and the second polarization state including the even channels (i.e. channels 2, 4, . . . n). Likewise polarized beam 107, which is the polarization transformation of beam 104, the first polarization state includes even channels of the input signal 101, and the second polarization state includes the odd channels of the input signal 101. It is important to note that second element 105 also increases the channel spacing (e.g. the frequency spacing) of the channels, illustratively by a factor of two. Next, a third element 108 combines the odd channel polarization vectors of beam 106 with the odd channel polarization vectors of beam 107, and directs the optical beam to odd output 109. Moreover, third element 108 combines the even channel polarization vectors of beams 106 and 107 and directs them to an output port 110.

As can be appreciated from a review of FIG. 1, the input signal 101, having a first channel spacing, undergoes a transformation by the interleaver 100 into two output ports (109, 110), each of which having channels with a second channel spacing that is twice that of the first channel spacing. Moreover, outputs 109 and 110 could become the input ports of a second concatenated interleaver/deinterleaver (not shown) which is similar to interleaver 100, and the channel spacing could be increased by another factor of two. Of course, further interleavers/deinterleavers (i.e. a third and/or fourth and so on) could be concatenated, with each increasing the channel spacing by a factor of 2. It is further noted that the outputs 109 and 110 could also be selectively coupled to other devices such as demultiplexers and optical add/drops.

Figure 2:
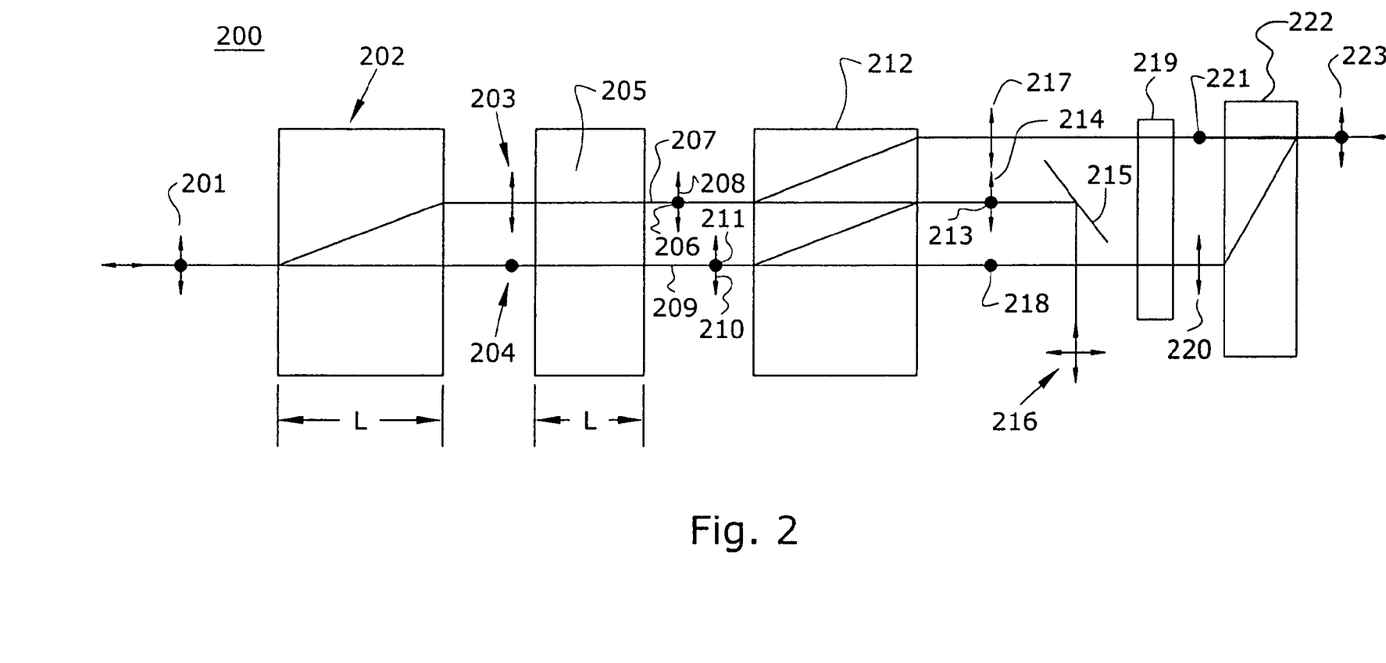
FIG. 2 is a schematic view of an interleaver according to another exemplary embodiment of the present invention.

Turning to FIG. 2, an interleaver/deinterleaver 200 (hereinafter referred to as interleaver 200) according to another exemplary embodiment of the present invention is described. An input optical signal 201 is illustratively from an optical fiber (not shown). The input signal 201 is illustratively elliptically polarized, which is a fair generalization since the polarization state of an optical beam can change as it traverses an optical fiber due to factors such as stress-induced birefringence. Input signal 201 is comprised of multiplexed optical wavelength channels, with each channel having a characteristic center wavelength (and thereby frequency). Each channel may also have a particular spread or sub-band, and the individual channels are separated by a particular channel spacing. By convention, this channel spacing refers to a channel center wavelength-to-channel center wavelength for adjacent channels.

For purposes of illustration, channel spacing (which may be in units of frequency period or spacing) between the individual channels in the multiplexed input signal is within a chosen ITU grid. The channel spacing (in this case frequency spacing) may be 400 GHz, 200 GHz, 100 GHz, 50 GHz or 25 GHz corresponding to channel center wavelength spacing of 3.2 nm, 1.6 nm or 0.8 nm, 0.4 nm and 0.2 nm, respectively.

Of course, the above referenced specifications of channel spacing are merely illustrative and are not intended to be in any way limiting of the application of the invention. To this end, as would be readily understood by one of ordinary skill in the art, the number of channels is basically limited to the total bandwidth of an amplifier used in the optical system. For example, this bandwidth limitation would be the bandwidth limitation of an amplifier such as an erbium doped fiber amplifier (EDFA). Illustrative wavelength channels are the C-band, which has typical channel wavelengths between 1528 nm and 1560 nm, and the L-band, which has typical channel wavelengths from 1565 nm to 1620 nm. Of course, the useful bandwidth for each channel is generally less than the spacing between each of the channels. Finally, it is noted that the interleaver 200 of the exemplary embodiment of the present disclosure may be incorporated into a synchronous optical network (SONET network), which complies with the OC-48 standard (2.5 Gb), the OC-192 standard (10 Gb) or the OC-768 standard (40 Gb). Of course, applications of the present invention to these standards are merely illustrative, and other standard optical networks within the purview of one having ordinary skill in the art can benefit from the use of the present invention.

The input optical signal 201 is incident perpendicularly to the end face of the first polarization splitter 202, which is illustratively a birefringent material such as rutile, calcite and yttrium vanadate ($YVO_4$). For reasons discussed more fully below, the birefringence, the magnitude of the difference between the ordinary and extraordinary indices of refraction, is usefully as great as possible. In the illustrative case where yttrium vanadate is used, the birefringence is on the order of 0.211 at a center wavelength of 1550 nm.

The first polarization splitter 202 fosters polarization diversity and, ultimately enables the interleaver 200 of the present invention to function substantially independently of the input polarization of the input optical signal 201. To this end, the input optical signal 201 may have a variety of polarization states; generally, it is elliptically polarized light. The first polarization splitter 202 separates the input optical signal 201 into its component polarization vectors (polarization states), which are then selectively transformed via the de-interleaving process as described herein. In this exemplary embodiment beam 203 is polarized parallel to the plane of the paper and beam 204 polarized perpendicularly to the plane of the paper.

In the exemplary embodiment shown in FIG. 2, the first polarization splitter 202 is a birefringent material having a principal plane oriented parallel to the top and bottom surfaces of the first polarization splitter 202. The input optical signal 201, being illustratively elliptically polarized, has two orthogonal electric field vectors, and components thereof oriented parallel to the extraordinary axis of the birefringent crystal will travel through the crystal at a faster (or slower, depending on the index of refraction, $n_e$) phase velocity than the electric field component oriented along the ordinary axis.

Thus, upon emerging from the first polarization splitter 202, the input optical signal 201 is split into two beams 203 and 204, with orthogonal polarization states. These polarization states are often referred to as s and p polarization states having a relative phase that is determined by the thickness and material properties (birefringence) of the first polarization splitter 202. The walk-off or spatial separation of the beams 203, 204 is dependent upon the length (L) of the first polarization splitter 202 and its birefringence, and should be large enough to prevent the beams 203, 204 from overlapping.

As discussed above, the input optical signal 201 is multiplexed having channels 1–n, and the channels have respective channel center wavelengths ($\lambda_1, \lambda_2, \ldots \lambda_n$). The first polarization splitter 202 merely splits the electric field vector of beam 201 into its orthogonal components, the polarization states of beams 203 and 204. It follows therefore that each beam (203 and 204) contains all of the channels. Beams 203,204, which each include odd and even channels, are then incident on polarization transforming (PT) element 205. PT element 205 is illustratively a birefringent crystal, such as calcite, rutile or yttrium vanadate. The physical properties that are desirable in element 205 are its optical anisotropies for effecting the polarization transformation of beams 203,204.

As will become clearer as the present description proceeds, the polarization transformation of beams 203, 204 by birefringent element 205 is useful in deinterleaving the input optical signal 201 into output optical signals having a channel spacing that is twice that of the channel spacing of the input optical signal. Accordingly, it is the anisotropic optical properties of element 205 which are useful to achieving this desired end. As such, while PT element 205 is illustratively a birefringent crystal, PT element 205 may be a known phase retarder. Moreover, it is noted that various optically anisotropic materials could be used as element 205. These include, but are not limited to, known electro-optic elements and birefringent optical fiber.

In the interest of simplicity of discussion, only the polarization transformation of beam 203 will be discussed in detail. The physics of the polarization transformation of beam 204 is the same, of course. Beam 203 is linearly polarized light having components that are in the plane of the paper as shown in FIG. 2. As described above, the input optical signal 201 is multiplexed having channels 1–n, and the channels have respective channel center wavelengths ($\lambda_1, \lambda_2, \ldots \lambda_n$); and accordingly, the beam 203 has polarization components representing each of these channels as well. In the illustrative embodiment, the PT element 205 is a birefringent crystal having its principal section and c-axis oriented diagonally (at a 45° angle) relative to the end faces of the crystal. Stated differently, the c-axis of element 205 is oriented at a 45° angle relative to the ordinary (o) and the extraordinary (e) axes. As such the c-axis is at a 45° angle to the plane of polarization of beam 203. Accordingly, linearly polarized light such as beam 203 will emerge as elliptically polarized light from the crystal. The benefit derived from the birefringence is the phase separation of the polarization vectors corresponding to the individual channels 1–n within the beam 203.

As discussed below, the phase separation between successive channels is dependent on the thickness (or length, L) of the birefringent material and the index of refraction differential between the ordinary and extraordinary axes. In the illustrative embodiment shown generally in FIG. 2, this phase differential between the successive channels is $\pi$. Accordingly, channel 2 having a center channel wavelength $\lambda_2$ has a polarization vector upon emerging from the PT element 205 that has a relative phase of $\pi$ radians with respect to the polarization vector of channel 1, having a center wavelength $\lambda_1$. Thereby, the first polarization splitter 202 effectively separates the channels in beam 203 so that the odd channels have co-linear polarization vectors (i.e. linearly polarized parallel or anti-parallel to one another) and the even channels have co-linear polarization vectors.

In the illustrative embodiment shown in FIG. 2, the odd channels 206 of beam 207 have polarization vectors that are perpendicular to the plane of the paper, while the even channels 208 of beam 207 have polarization vectors that are in the plane of the paper. By similar analysis, beam 209, which is the polarization transformation of beam 204, has odd channels 210 with polarization states in the plane of the paper and even channels 211 with polarization states perpendicular to the plane of the paper.

The beams 207, 209 of elliptically polarized light having orthogonal polarization vectors of even and odd channels therein are then impingent upon the second polarization splitter 212. Illustratively, second polarization splitter 212 is a birefringent material having the same thickness, optic axis orientation, and index difference between the ordinary and extraordinary axes as first polarization splitter 202. As such, the odd channels 206 from beam 207 emerge undisplaced from the second polarization splitter 212 as beam 213 having the polarization state shown. The odd channels 210 of beam 209, being linearly polarized vectors in the plane of the paper are displaced due to the birefringence of the second polarization splitter 212. Shown as beam 214 with polarization states in the plane of the paper, these odd channels along with odd channels of beam 213 are then reflected by reflective element 215 and form the odd channel output signal 216.

Similarly, the beam 207 has polarization components 208 that are oriented in the plane of the paper and are displaced by the birefringent second polarization splitter 212.

These are the even channels 217 having polarization vectors as shown. The even channels of beam 209 having polarization vectors 211 traverse second polarization splitter 212 undisplaced and emerge as beam 218 having vector components as shown.

A half wave plate (or compensator) 219 rotates the polarization states of beams 217 and 218 so as to minimize polarization mode dispersion. In the exemplary embodiment of FIG. 2, the half-wave plate 219 is illustratively an achromatic quartz half-wave plate. Orthogonally polarized beams 220 and 221, containing the even channels then traverse birefringent element 222, with beam 221 being displaced and combined with undisplaced beam 220 to form the even channel output signal 223. (It is noted that herein, the second polarization splitter 212, the reflective element 215, the half wave plate 219 and the birefringent element 223 may be referenced as a combining element).

As can be appreciated from a review of FIG. 2, the input signal 201, having a first channel spacing, undergoes a transformation by the interleaver 200 into odd and even output signals 216 and 223, respectively, each of which have channels with a second channel spacing that is twice that of the channel spacing of input signal 201. Odd output signal 216 could be input to a concatenated interleaver/deinterleaver (substantially the same as interleaver 200), and the channel spacing could be increased by another factor of two. Likewise, this could be accomplished using even output signal 223 as the input of a concatenated interleaver/deinterleaver. Of course this concatenation can continue, with each successive interleaver further increasing the channel spacing by a factor of two. It is further noted that the odd and even output signals 216 and 223 could also be selectively coupled to other devices such as demultiplexers and optical add/drops.

In the illustrative embodiment shown in FIG. 2, the de-interleaving which illustratively doubles the first channel spacing of the input signal exploits the anisotropic optical properties of element 205. Moreover, the element 205 is illustratively a birefringent crystal having ordinary and extraordinary axes. In the exemplary embodiment of FIG. 2, the polarization vectors of beams 203 and 204 are in mutually orthogonal polarization states. The c-axis of birefringent element 205 is oriented at 45 relative to each of these polarization states. As such, it can be shown that for beam 203 having the polarization state described above, the transmittance (at the output of PT element 205) is given by:

$$T = \left(\frac{1}{2}\right)[1 + \cos(\phi_0 + 2\pi\upsilon\tau)] \qquad \text{eqn. (1)}$$

Where $\upsilon$ is the relative optical frequency of a particular channel, $\phi_0$ is a phase constant, and $\tau$ is the temporal delay between the extraordinary and ordinary polarization vectors, given by:

$$\tau = \left(\frac{L}{c}\right)(n_e - n_o) = \left(\frac{L}{c}\right)(\Delta n_g) \qquad \text{eqn. (2)}$$

where L is the length of the crystal (in this case PT element 205), c is the speed of light in vacuum, and $\Delta n_g$ is the group index of refraction difference between the ordinary and extraordinary indices of refraction for the center wavelength of the particular channel. Of course a similar analysis would hold for beam 204, and is forgone at this point in the interest of brevity and clarity of discussion.

The resultant temporal delay, $\tau$, between the extraordinary and ordinary beams is exploited in the present invention. To this end, (again the discussion will focus only one beam in the interest of simplicity), the odd channels 206 and the even channels 208, have a relative temporal delay $\tau$ as a result of traversing the crystal 205. This delay is manifest in the optical transmission coefficient for elliptically polarized beam 208. The frequency period or spacing of the sinusoidal transmission coefficient given by (1) above is $$\left(\frac{1}{\tau}\right).$$

Accordingly, odd channels 206 and even channels 208 have a channel spacing of $$\left(\frac{1}{\tau}\right).$$

It follows therefore, that after recombination of the of odd channels (which are in orthogonal polarization (temporally retarded) states due to the birefringent properties of crystal 205) the channel spacing of the output signal at odd channel output port 216 is also $$\left(\frac{1}{\tau}\right),$$

twice that of the channel spacing of the input channel 201, which is $$\left(\frac{1}{2\tau}\right).$$

Thus, in the illustrative embodiment of the present invention, the input optical signal 201 has a channel frequency spacing of $$\left(\frac{1}{2\tau}\right),$$

while the odd and even output signals 216 and 223, respectively each have a channel frequency spacing of $$\left(\frac{1}{\tau}\right).$$

The increase in channel spacing at the output will afford benefits in optical communication systems. A similar analysis follows for the output signal at even channel output port 223.

In the illustrative embodiment of FIG. 2, the channel spacing (frequency spacing) that results from the birefringent characteristics of crystal 205 can be chosen by picking the length of the crystal, L, for a particular birefringent crystal 205. Moreover, the frequency spacing or free spectral range FSR is given by $$\left(\frac{1}{\tau}\right).$$

Thus, the FSR can be set by the selection of the crystal length, L, for a particular crystal. Finally, the center wavelength or frequency of the channels can be set by selection of $\phi_0$ in (1) above. This can aid in fine-tuning the embodiment of FIG. 2 to a standard channel grid, such as an ITU grid mentioned above.

As referenced previously, in many instances, adverse environmental effects can have a deleterious impact on the performance of optical devices. In accordance with another exemplary embodiment of the present invention a method and apparatus for interleaving/de-interleaving optical signals includes a passive thermal compensator. The passive thermal compensator enables the apparatus to operate over a predetermined temperature range with substantially no temperature induced frequency (and, thereby, wavelength) drift of the output signal.

Figure 3:
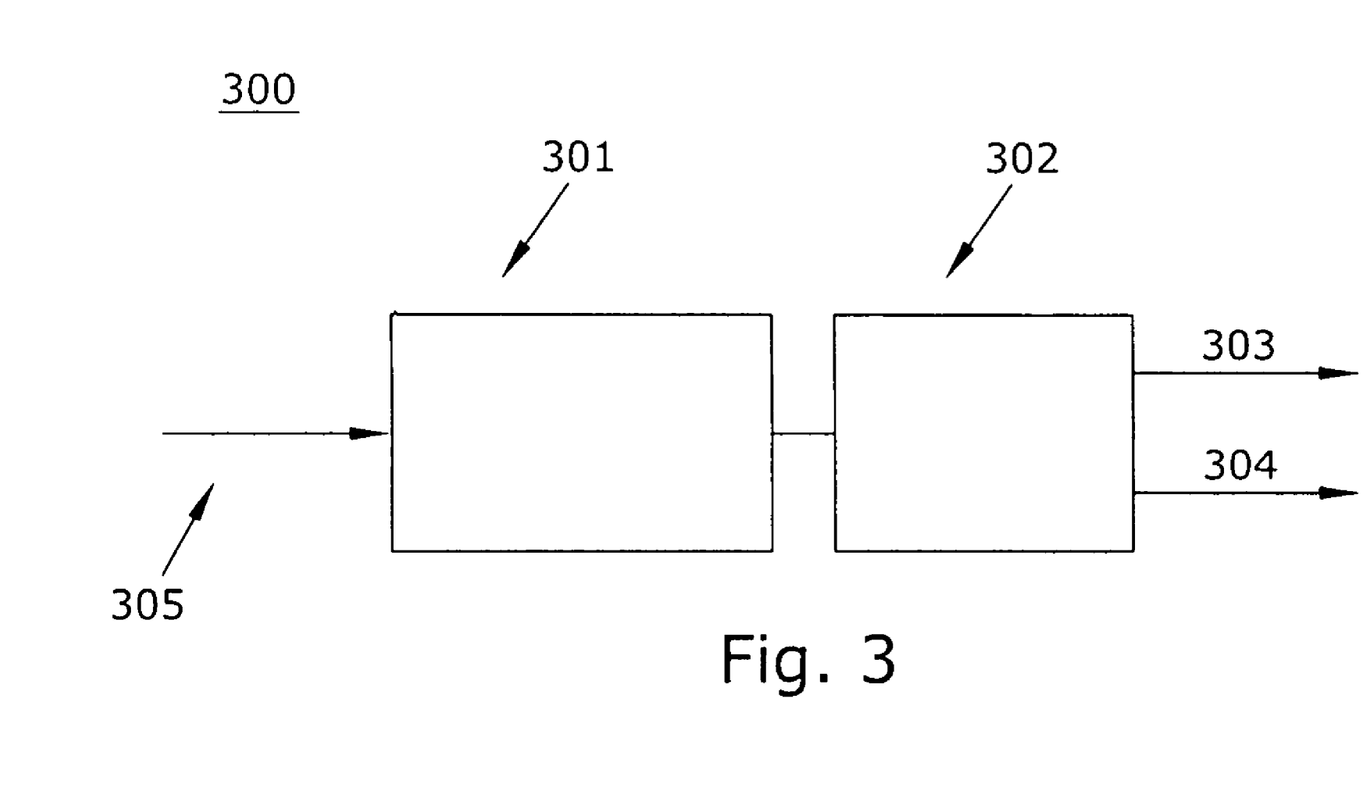
FIG. 3 is a schematic representation of an interleaver according to another exemplary embodiment of the present invention.

Turning initially to FIG. 3, an optical device 300 in accordance with an illustrative embodiment of the present invention is shown. An input signal 305 is incident on an interleaver/deinterleaver 301 (hereinafter referred to as interleaver 301). The input signal 305 is a WDM optical signal illustratively having channels 1, 2, . . . n with respective channel center wavelengths of $\lambda_1, \lambda_2, \ldots \lambda_n$. Output signals 303, 304 are deinterleaved, and have a channel spacing that is an integral multiple of the channel spacing of the input signal 305.

In the exemplary embodiment of FIG. 3, the interleaver 301 includes at least one birefringent element, which is used to separate the polarization states of the input signal 305 into orthogonal polarization components. As is described in greater detail herein, ambient temperature affects both the optical path length and the birefringence of birefringent elements. Accordingly, it is beneficial to compensate for changes in the ambient temperature, which can adversely impact the optical signal, and to do so in a passive manner.

A passive thermal compensator 302 according to an illustrative embodiment of the present invention compensates for thermal effects (e.g., ambient thermal effects) so that the output signals 303, 304 of the optical device 300 experience substantially no temperature-induced frequency/wavelength drift compared to the input optical signal 305. According to an illustrative embodiment of the present invention, the passive thermal compensator 302 includes at least one birefringent element, which compensates for temperature-induced frequency or wavelength shift of the input signal 305 that is caused by thermal influences on the interleaver/deinterleaver 301.

Accordingly, the output signals 303 and 304 (deinterleaved signals in this illustrative embodiment) are substantially unaffected by variations in the ambient temperature over a predetermined range. As such, fluctuations in the optical network ambient temperature, which may result from internal and external components of the optical network, are compensated for by virtue of the passive thermal compensator 302 without the necessity for ambient temperature controls, such as cooling elements. Moreover, as will become clearer as the present description proceeds, the passive thermal compensator 302 in accordance with the present exemplary embodiment compensates/corrects for thermal effects rather than attempts to prevent them as an active ambient temperature controller would.

Figure 4:
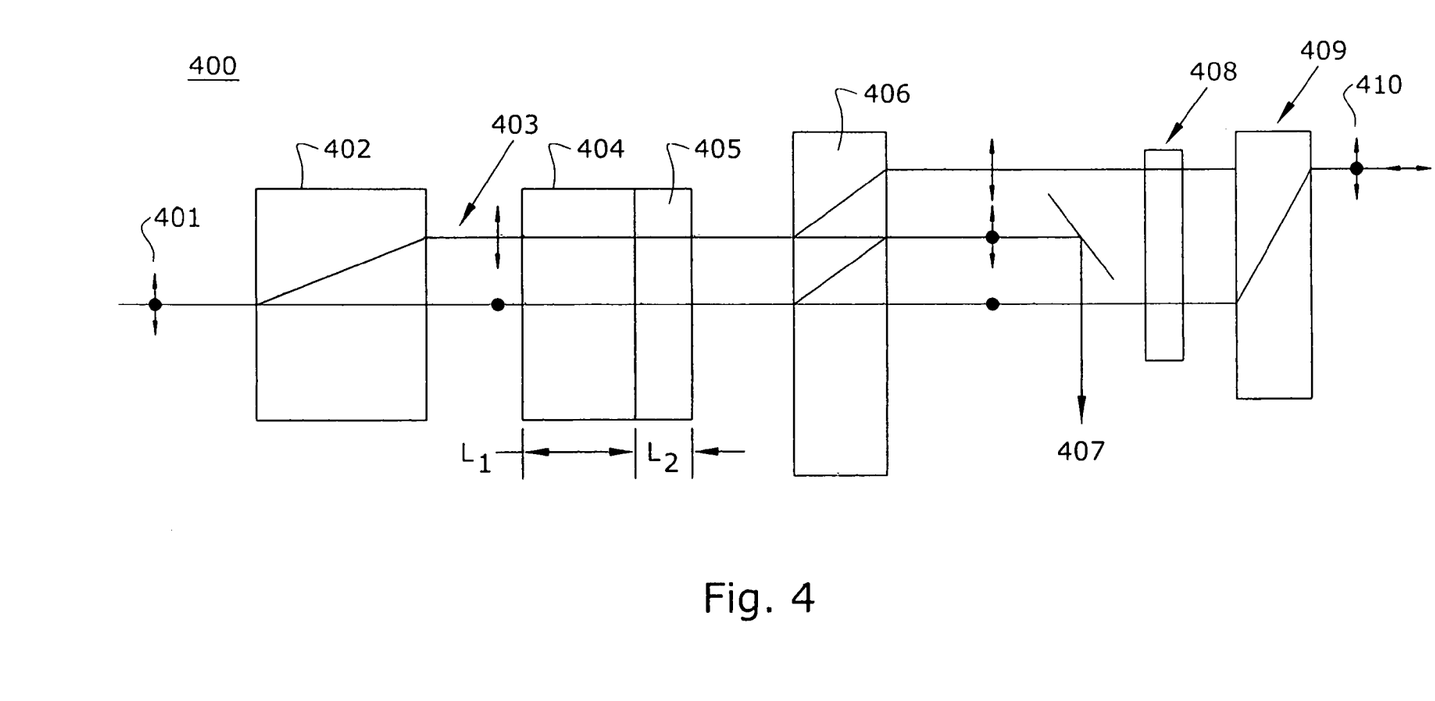
FIG. 4 is a block diagram of an interleaver according to an exemplary embodiment of the present invention.

FIG. 4 shows another illustrative embodiment of the invention of the present disclosure. An interleaver/deinterleaver 400 (hereinafter referred to as interleaver 400) is illustratively based on polarization interferometry using birefringent materials and includes a passive thermal compensator. It is noted that many of the details of deinterleaving of the input optical signal 401 are substantially identical to those described in connection with the exemplary embodiment of FIG. 2. As such, many of these details may not be repeated in the interest of brevity.

An input signal 401 is incident perpendicularly to the end face of the polarization splitter 402, which illustratively includes a birefringent material such as rutile, calcite or yttrium vanadate (YVO$_4$). The polarization splitter 402 fosters polarization diversity, and ultimately enables the interleaver 400 to function independently of the polarization of the input signal 401. The polarization splitter 402 splits the input signal 401 into two beams 403. These two beams 403 have orthogonal polarization states, which are often referred to as s and p polarization states having a relative phase that is determined by the thickness and material properties (birefringence) of the polarization splitter 402. The input optical signal 401 is multiplexed having channels 1, 2, ... n, and the channels have respective channel center wavelengths $\lambda_1, \lambda_2, \ldots \lambda_n$. The polarization splitter 402 merely splits the electric field vector of input signal 401 into its orthogonal components, the polarization states of beams 403. It follows, therefore that each of the beams 403 contain all the channels.

Next, beams 403 are incident upon polarization transforming (PT) element 404. In the illustrative embodiment, PT element 404 is a birefringent crystal, such as calcite, rutile, or (YVO$_4$). It is noted that PT element 404 may also be a known phase retarder. The physical properties that are desirable in PT element 404 are its optical anisotropies for effecting the polarization transformation of beams 403. Ultimately, the optical properties of element 404 are useful in de-interleaving the input signal 401 into output optical signals having a channel spacing that is twice that of the channel spacing of the input signal 401.

It is noted again that other anisotropic materials such as those referenced above may be used for PT element 404. Moreover, in the illustrative embodiment shown in FIG. 4, element 404 is a birefringent crystal having its principle section and c-axis oriented diagonally (at a 45° angle) relative to end phases of the crystal. As such, the c-axis is at 45° angle relative to the plane of polarization of the beams 403.

In the illustrative embodiment shown in FIG. 4, the channel separation that ultimately enables the de-interleaving of the input optical signal, exploits the anisotropic optical properties of PT element 404. Moreover, PT element 404 is illustratively a birefringent crystal having ordinary and extraordinary axes. In the exemplary embodiment of FIG. 4, the polarization vectors of beams 403 are in mutually orthogonal polarization states. The c-axis of birefringent element 404 is oriented at 45° relative to each of these polarization states. For beams 403 having the polarization state described above, the transmittance of beam 407 (odd channels) is given by equation (1) above. Again, τ is the temporal delay between the ordinary and extraordinary polarization vectors and is given by eqn. (2). Moreover, 1−T is transmitted by beam 410 (even channels) after its combination by elements 406, 408 and 409.

The temporal delay, τ, between the extraordinary and ordinary beams is exploited to effect the desired channel spacing in the de-interleaving of the input signal 401. However, as mentioned briefly above, the temperature of birefringent elements (such as element 404) may affect both the length and indices of refraction of the birefringent element. Ultimately, because the channel spacing is related to the temporal delay τ, the channel spacing may also be adversely impacted by the effect of temperature on the optical path length and birefringence.

Quantitatively, the temperature induced frequency shift of element 204 is given by:

$$\frac{\partial f}{\Delta T} = \frac{c}{\lambda \Delta n_g}\left(\frac{d\Delta n}{dT} + \Delta n\alpha\right), \qquad \text{eqn. (3)}$$

where, $$\frac{d\Delta n}{dT} = \frac{dn_e}{dT} - \frac{dn_o}{dT}, \qquad \text{eqn. (4)}$$

α is the thermal expansion coefficient of element 404, λ is the wavelength and f is the relative optical frequency.

Illustratively, using known material properties of YVO$_4$, the temperature induced wavelength drift is on the order of approximately −4.2 GHz/° C. This is, unfortunately, on the order 5 times the temperature drift of an uncompensated fiber Bragg grating, which may be used in the de-interleaving of a WDM/DWDM signal. In order for WDM/DWDM devices based on anisotropic optical elements such as birefringent crystals to be practical in deployed optical systems, it is important to reduce the thermal drift either by active temperature control (such as climate control elements) or by passive compensation. As discussed above, active temperature control techniques have certain drawbacks making the passive compensation technique of the present invention an attractive alternative to active control of the ambient temperature.

As stated above, the thermal effects on the birefringent elements such as PT element 404 are generally manifest in a change in the length (L) of the PT element 404 as well as a change in indices of refraction along the ordinary and extraordinary axes. These thermal effects must be compensated for, as a temperature induced change in these parameters ultimately affects the temporal delay τ, the free spectral range (FSR), and the channel spacing. According to illustrative embodiments of the present invention, the thermal compensation is effected passively, incorporating a compensating anisotropic optical element such as passive thermal compensating (PTC) element 405 to effect temperature compensation. Moreover, PTC element 405 is adjacent PT element 404 and elements 404 and 405 are illustratively birefringent materials, which are adhered to one another by suitable adhesive. As such, PT element 404 and PTC element 405 behave substantially as one optical element.

As stated, an object of the present invention is to minimize the temperature induced wavelength drift. Accordingly, one objective of the present invention is that the temperature induced frequency shift of element 404 is nullified. Quantitatively, this means that eqn. (3) is zero:

$$\frac{\partial f}{\Delta T} = O \qquad \text{eqn. (5)}$$

In the exemplary embodiment of FIG. 4, where a compensating element such as PTC element 405 is used to achieve passive thermal compensation, it can be shown that thermal compensation requires:

$$L_1 \frac{d\Delta n_1}{dT} + L_2 \frac{d\Delta n_2}{dT} + \Delta n_1 L_1 \alpha_1 + \Delta n_2 L_2 \alpha_2 = O \qquad \text{eqn. (6)}$$

where $L_1$ is the length of PT element 404, $L_2$ is the length of element 405, $\Delta n_1$ is the birefringence of element 404, $\Delta n_2$ is the birefringence of element 405, $\alpha_1$ is the expansion coefficient of element 404 and $\alpha_2$ is the expansion coefficient for element 405. This is referred to as the condition of athermalization.

Other objectives of the passive thermal compensation of the present invention are to maintain the channel spacing, the temporal delay υ, and free spectral range (FSR) across a particular temperature range. The temporal delay, τ, of birefringent elements 404 and 405 are additive. As such:

$$\tau = \tau_1 + \tau_2 \qquad \text{eqn. (7)}$$

so $$\tau = \frac{L_1}{c}(\Delta n_1) + \frac{L_2}{c}(\Delta n_2) \qquad \text{eqn. (8)}$$

where $\tau_1$ and $\tau_2$ are the temporal delays resulting from birefringent elements 404 and 405, respectively.

Because the temperature dependence of the indices of refraction of the birefringent elements, as well as the expansion coefficients $\alpha_1$, $\alpha_2$ of elements 404 and 405, respectively, are known, in order to satisfy the above relations of eqn. (6) and (8), it is necessary to determine the suitable lengths $L_1$ and $L_2$ for the particular materials chosen for birefringent elements 404 and 405. Practically, this requires determining the ratio of $$\frac{L_1}{L_2}$$

from eqn. (6), the condition for athermalization. Accordingly, once this ratio is determined, the interleaver 400 is passively athermalized for a variety of free spectral ranges (FSR), and channel spacing. Stated differently, when the ratio of the lengths of elements 404 and 405 is determined from eqn. (6), the interleaver 400 according to an illustrative embodiment of the invention of the present disclosure is athermalized for free spectral ranges and channel spacings of interest. It follows of course that if it is desired to have an athermalized interleaver with a particular free spectral range/channel spacing, it is necessary to determine the appropriate ratio of the lengths of elements 405 and 405. Illustratively, the interleaver 400 may interleave/deinterleave optical signals having free spectral ranges (and channel spacings) of 400 GHz, 200 GHz, 100 GHz, 50 GHz and 25 GHz, and 12.5 GHz in an athermalized manner.

It is noted that according to the presently described exemplary embodiment, the fast axes of PT element 404 and PTC element 405 should be either perpendicular or parallel to one another. If the fast axis of PT element 404 were oriented at an angle between 0° and 90°, and multiples thereof, the output would not be the same as the ideal situation where there is no need to compensate for thermal effects with element 405. To this end, if the fast axes of the PT element 404 and PTC element 405 are not oriented parallel or perpendicular to one another, the phase delay between the extraordinary and ordinary rays will result in harmonics and the output will not be the desired output, which is illustratively the deinterleaved output signal described in the parent application.

According to an illustrative embodiment of the present invention, the crystal that may be used for PTC element 405 has a fast axis, which is parallel to the fast axis of PT element 404, which is also illustratively a birefringent crystal. Moreover, the crystal should be chosen so that $$\frac{d\Delta n_2}{dT} \text{ and } \frac{d\Delta n_1}{dT}$$

have opposite signs. Since $$\frac{d\Delta n_1}{dT}$$

is usually the dominating term, it is possible to cancel the thermal affect while the birefringence of the second crystal is merely additive to that of the first crystal. In this particular embodiment, the length of the PT element 404 (also referred to as the dominating element) is shorter than the birefringent element of the uncompensated interleaver, as described in the parent application. Again, this is because the birefringence is additive in this particular embodiment. Accordingly, the above described embodiment enables the passive compensation for thermal effects by determination of the lengths $L_1$ and $L_2$, which satisfy the relation of eqn. (6).

Alternatively, the fast axes of PT element 404 and PTC element 405 may be orthogonal. Accordingly, the fast axis of the first element 404 will be parallel to the slow axis of element 405. In this case, and particularly when yttrium vanadate ($YVO_4$) is used for birefringent elements 404 and 405, $$\frac{d\Delta n_2}{dT}$$

has the same sign as $$\frac{d\Delta n_1}{dT}, \text{ but } \frac{\Delta n_1}{\Delta n_2} \gg \frac{\frac{d\Delta n_1}{dT}}{\frac{d\Delta n_2}{dT}}.$$

As such, not only does the second birefringent element 405 compensate for the thermal effect, but it also reduces the amount of birefringence provided by the first element 404. This partial cancellation of the birefringence of the first element 404 by the second element 405 necessitates, of course, that the first element 404 has a greater length ($L_1$) than in the case in which there is no compensation for thermal effects. By solving the condition for athermalization as set forth in eqn. (6), the ratio of the lengths $$\left(\frac{L_1}{L_2}\right)$$

PT element 404 to the PTC element 405 may be determined. Moreover, by solving eqn. (6) and (8,) the lengths $L_1$ and $L_2$ for elements 404 and 405, respectively, for particular materials, temporal delay, FSR and channel spacing may be determined in absolute value. Suitable materials such as lithium niobate (LiNbO₃) may be used for element 405 in this illustrative embodiment, with YVO₄ illustratively being used as the material for PT element 404. Of course, the materials used for elements 402, 404, 405 and 406 could be other anisotropic optical elements such as those described previously.

As can be readily appreciated, the embodiment shown in FIG. 4 provides passive thermal compensation to a WDM optical link. Depending upon applications, residual temperature drift in WDM optical link based on polarization interferometry may be required to be less than approximately ±1 GHz over an illustrative temperature range of approximately −5° C. to approximately +70° C. This is an improvement on the order of approximately a factor of 170 compared to an uncompensated polarization interferometry based WDM, and is comparable to the performance of a fiber Bragg grating (FBG) based interleaver.

Figure 5:
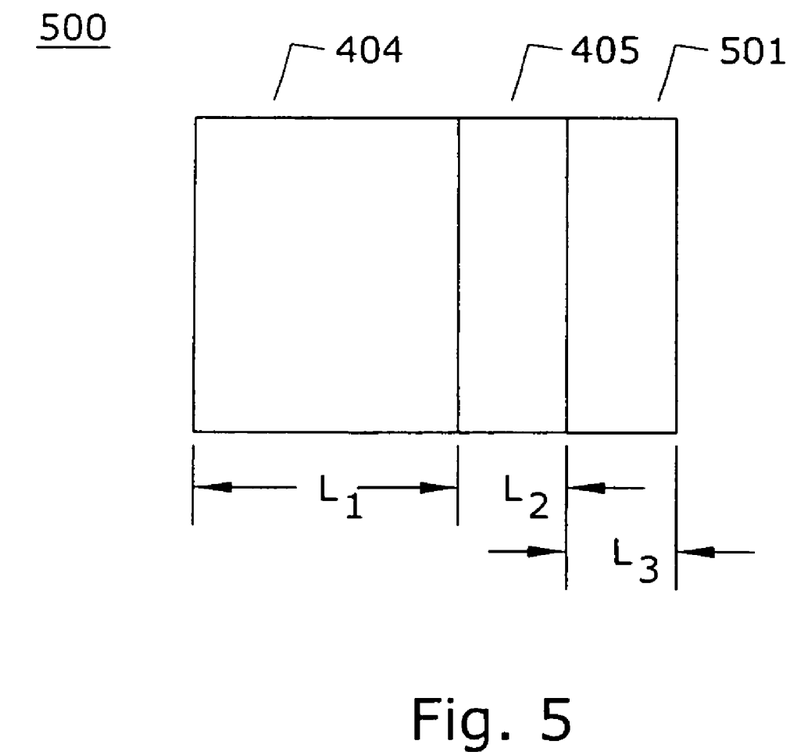
FIG. 5 is a block diagram of an interleaver according to another exemplary embodiment of the present invention.

In some circumstances, it may be desirable to compensate for second order temperature effects. According to an exemplary embodiment, this may be carried out using an additional PTC element. Such an element is shown in FIG. 5 at 501. To this end, element 500 includes PT element 404, and PTC element 405 of FIG. 4 as well as another PTC element 501. The basic teachings of FIG. 4 apply to FIG. 5, and the other elements of the interleaver 400 of FIG. 4 have been forgone in FIG. 5 in the interest of clarity of discussion. (Of course, element 500 would be located between element 402 and element 406 in interleaver 400).

For precise passive thermal compensation a detailed knowledge of the thermal properties of elements 404, 405 and 501 is useful. Fortunately, the interleaver 400 shown generically in FIG. 4 is a very good temperature sensor. By measuring the temperature dependence of the frequency (wavelength) on shift in a polarization independent interleaver 400, which contains at least one birefringence element, higher order temperature coefficients can be derived. As such, the second order elements can be used in combination with the first order elements and the basic equation for the temporal delay, 'τ in order to determine the suitable ratios for the lengths ($L_1$, $L_2$, $L_3$) of elements 404, 405 and 501, respectively, for various materials used in these capacities. Quantitatively, it can be shown that:

$$\tau = \frac{L_1}{C}(\Delta n_1) + \frac{L_2}{C}(\Delta n_2) + \frac{L_3}{C}(\Delta n_3) \qquad \text{eqn. (9)}$$

$$L_1 \frac{d(\Delta n_1 \alpha_1)}{dT} + L_2 \frac{d(\Delta n_2 \alpha_2)}{dT} + L_3 \frac{d(\Delta n_3 \alpha_3)}{dT} = O \qquad \text{eqn. (10)}$$

$$L_1 \frac{d^2}{dT^2}(\Delta n_1 \alpha_1) + L_2 \frac{d^2}{dT^2}(\Delta n_2 \alpha_2) + L_3 \frac{d^2}{dT^2}(\Delta n_3 \alpha_3) = O \qquad \text{eqn. (11)}$$

where $L_3$, $\Delta n_3$, $\alpha_3$ are the length, birefringence, and expansion coefficient, respectively, of the third element 501. Finally, the orientation of the fast axes of elements 404, 405 and 501 described above are illustrative. As would readily be appreciated by one of ordinary skill in the art having had the benefit of the present disclosure, the orientation of the fast axes of elements 404, 405 and 501 can be a variety of permutations of parallel and perpendicular orientations. While not particularly spelled out in the present invention, these are, of course, within the scope of the present invention.

The invention having been described in detail in connection through a discussion of exemplary embodiments, it is clear that various modification of the invention will be apparent to one of ordinary skill in the art having had the benefit of the present disclosure. Such variations and modification are included within the scope of the appended claims.

The invention claimed is:

1. An optical device, comprising:
an interleaver/deinterleaver having at least one polarization transforming element coupled to a first passive thermal compensator and a second passive thermal compensator, the thermal compensators configured to substantially compensate, respectively, for first order and second order temperature-induced frequency drift of the at least one polarization transforming element over a desired temperature range.

2. The optical device of claim 1, wherein at least one thermal compensator includes at least one birefringent element.

3. The optical device of claim 2, wherein the at least one polarization transforming element includes at least one birefringent element.

4. The optical device of claim 3, wherein the at least one birefringent element of the polarization transforming element has a fast axis, and the at least one birefringent element of the thermal compensator has a fast axis, and the fast axes are parallel.

5. The optical device of claim 3, wherein the at least one birefringent element of the polarization transforming element has a fast axis, and the at least one birefringent element of the thermal compensator has a fast axis, and the fast axes are orthogonal.

6. The optical device of claim 3, wherein the optical device satisfies a condition of athermalization given by:

$$L_1 \frac{d\Delta n_1}{dT} + L_2 \frac{d\Delta n_2}{dT} + \Delta n_1 L_1 \alpha_1 + \Delta n_2 L_2 \alpha_2 = O$$

where $L_1$ is a length of the at least one birefringent element of the polarization transforming element, $L_2$ is a length of the at least one birefringent element of the thermal compensator, $\Delta n_1$ is the birefringence of the at least one birefringent element of the polarization transforming element, $\Delta n_2$ is the birefringence of the at least one birefringent element of the thermal compensator, $a_1$ is an expansion coefficient of the at least one birefringent element of the polarization transforming element, and $a_2$ is the expansion coefficient of the at least one birefringent element of the thermal compensator.

7. The optical device of claim 2, wherein the at least one birefringent element of the passive thermal compensator is chosen from the group consisting essentially of rutile, calcite, lithium niobate, and yttrium vanadate.

8. The optical device of claim 1, wherein an interleaved/deinterleaved optical signal includes channels having a spacing in the range of approximately 12.5 ghz to approximately 400 ghz when outputted from the optical device.

9. The optical device of claim 8, wherein the temperature induced frequency drift is in the range of approximately −2.5 ghz to approximately +2.5 ghz.

10. An optical device, comprising:
an interleaver/deinterleaver having at least one polarization transforming element directly attached to at least one passive thermal compensator, wherein an optical signal which traverses the optical device undergoes substantially no temperature-induced frequency drift over a desired temperature range and wherein the thermal compensator includes at least two birefringent elements that are directly attached to one another and one of the at least two birefringent elements is directly attached to the birefringent element of the polarization transforming element.

11. The optical device of claim 10, wherein the temperature induced frequency drift is in the range of approximately −2.5 GHz to approximately +2.5 GHz.

12. The optical device of claim 10, wherein the desired temperature range is approximately −10° C. to approximately +70° C.

13. The optical device of claim 10, wherein the optical signal includes mxn channels when inputted into the optical device, and includes n/m output channels when outputted from the optical device, wherein m and n are integers.

14. The optical device of claim 13, wherein m=2.

15. A method of interleaving/deinterleaving an optical signal, the method comprising:
    providing an interleaver/deinterleaver having at least one polarization transforming element directly attached to at least one passive thermal compensator, wherein the passive thermal compensator comprises at least two birefringent elements directly attached to one another and one of the at least two birefringent elements is directly attached to the polarization transforming element; and
    traversing the interleaver/deinterleaver with an optical signal, wherein the optical signal undergoes substantially no temperature-induced frequency drift over a desired temperature range.

16. The method as recited in claim 15, wherein the desired temperature range is approximately −10° C. to approximately +70° C.

17. A method of interleaving/deinterleaving an optical signal, the method comprising:
    providing an interleaver/deinterleaver having at least one polarization transforming element coupled to a first passive thermal compensator and a second passive thermal compensator; and
    traversing the interleaver/deinterleaver with an optical signal, wherein the thermal compensators are configured to substantially compensate, respectively, for first order and second order temperature-induced frequency drift of the at least one polarization transforming element over a desired temperature range.

18. The method of claim 17, wherein at least one thermal compensator includes at least one birefringent element.

19. The method of claim 18, wherein the at least one polarization transforming element includes at least one birefringent element.

20. The method of claim 19, wherein the at least one birefringent element of the polarization transforming element has a fast axis; the at least one birefringent element of the thermal compensator has a fast axis, and the fast axes are orthogonal.

21. The method of claim 19, wherein the at least one birefringent element of the polarization transforming element has a fast axis, and the at least one birefringent element of the thermal compensator has a fast axis, and the fast axes are parallel.

* * * * *